United States Patent

Mack et al.

[11] Patent Number: 5,489,583
[45] Date of Patent: Feb. 6, 1996

[54] 2-SUBSTITUTED 3-(4-AMIDINOPHENYL)PROPIONIC ACID DERIVATIVES

[75] Inventors: Helmut Mack, Meckenheim; Thomas Pfeiffer, Limburgerhof; Hans W. Hoeffken, Ludwigshafen; Hans-Joachim Boehm, Limburgerhof; Wilfried Hornberger, Ludwigshafen, all of Germany

[73] Assignee: BASF Aktiengesellschaft, Ludwigshafen, Germany

[21] Appl. No.: 170,357

[22] PCT Filed: Jun. 23, 1992

[86] PCT No.: PCT/EP92/01411

§ 371 Date: Dec. 28, 1993

§ 102(e) Date: Dec. 28, 1993

[87] PCT Pub. No.: WO93/01208

PCT Pub. Date: Jan. 21, 1993

[30] Foreign Application Priority Data

Jul. 3, 1991 [DE] Germany .................. 41 20 947.3

[51] Int. Cl.$^6$ ................. A61K 31/395; C07D 403/12
[52] U.S. Cl. ................ 514/183; 540/362; 540/463; 540/527; 546/216; 546/164; 546/146; 548/546; 514/210; 514/211; 514/212; 514/228.8; 514/235.2; 514/307; 514/311; 514/327; 514/408; 514/235.5
[58] Field of Search ................... 540/362, 463, 540/527; 546/216, 164, 146; 548/546; 514/183, 210, 211, 212, 228.8, 307, 311, 327, 408

[56] References Cited

FOREIGN PATENT DOCUMENTS 0236163  9/1987  European Pat. Off. .............. 514/183

OTHER PUBLICATIONS

Voigt et al. "Pharmazie" vol. 41 (1986) pp. 233–235.

Primary Examiner—Robert T. Bond
Attorney, Agent, or Firm—Keil & Weinkauf

[57] ABSTRACT

2-Substituted 3-(4-amidinophenyl)propionic acid derivatives of the formula

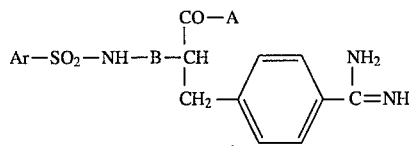

in which A, Ar and B have the meanings stated in the description, and the preparation thereof are described. The compounds are suitable for controlling diseases.

4 Claims, No Drawings

2-SUBSTITUTED 3-(4-AMIDINOPHENYL)PROPIONIC ACID DERIVATIVES

The present invention relates to novel 2-substituted 3-(4-amidinophenyl)propionic acid derivatives, the preparation thereof and the use thereof for controlling diseases.

Thrombin belongs to the group of serine proteases and plays a central part in the blood coagulation cascade as terminal enzyme. Both the intrinsic and the extrinsic coagulation cascade lead via several intensification states to the production of thrombin from prothrombin. The thrombin-catalyzed cleavage of fibrinogen then initiates blood coagulation and thus also possible thrombus formation. Thrombin additionally stimulates the aggregation of platelets which in turn, owing to the formation of platelet factor 3 and coagulation factor XIII as well as a whole series of highly active mediators, intensify thrombin formation.

The formation and action of thrombin are central events in the development both of white, arterial and of red, venous thrombi, and therefore potentially effective sites of attack of drugs. Thrombin inhibitors are, in contrast to heparin, able completely to inhibit, independently of cofactors, simultaneously the actions of thrombin both in the coagulation cascade and on platelets. They are able in the acute phase to prevent thromboembolic events after percutaneous transluminal coronary angioplasty (PCTA) and lysis and to act as anticoagulants in extracorporeal circulation (heart-lung machine, hemodialysis). They can also be used generally for thrombosis prophylaxis, for example after surgical interventions.

Two classes of compounds have to date been described as low molecular weight thrombin inhibitors, namely a) substances of the benzamidine type (DD 155,954, FR 2,593,812, FR 2,593,813, EP 236,164 and C.A. 113, (1990) 6182j) and b) substances of the arginine type (U.S. Pat. No. 4,258, 192, DE 2,801,478, EP 293,881, EP 185,390).

We have now found that 2-substituted 3-(4-amidinophenyl)propionic acid derivatives of the formula

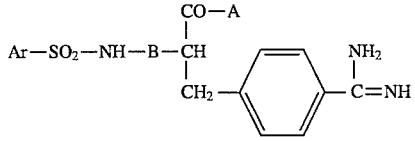

where

A is

or —OR³ in which R¹ and R², which can be identical or different, are each hydrogen, saturated or unsaturated alkyl with up to 6 carbons or aralkyl or aryl, or R¹ and R² together with the nitrogen to which they are bonded are a 5- to 7-membered saturated ring which is unsubstituted or substituted by alkyl radicals with up to 4 carbons and can contain an oxygen atom, where the nitrogen and oxygen atoms are in the 1,2 or 1,4 positions, and where R³ is hydrogen, saturated or unsaturated alkyl with up to 6 carbons, cycloalkyl or aralkyl, B is

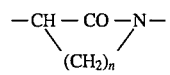

(where n is 1, 2, 3, 4 or 5) or

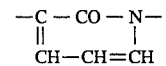

Ar is phenyl or α- or β-naphthyl which is unsubstituted or substituted by one or more halogen atoms, nitro groups, amino groups, $C_{1-4}$-mono- or bisalkylamino groups, hydroxyl groups, $C_{1-4}$-alkyl radicals, $C_{1-4}$-alkoxy groups, a methylenedioxy or ethylenedioxy radical, or Ar is pyridyl, quinolyl or isoquinolyl which is unsubstituted or substituted by one or more $C_{1-4}$-alkyl groups or $C_{1-4}$-alkoxy groups, and the salts thereof with physiologically tolerated acids have an improved action.

Preferred compounds are those where B is a pyrrolidinone, a piperidinone or a piperidone group, A is —NR¹R² where R¹ and R² together with the nitrogen atom are a 5- to 7-membered ring which may be substituted by $C_{1-4}$-alkyl radicals, and Ar is β-naphthyl which is substituted by one or more $C_{1-4}$-alkoxy radicals.

Particularly preferred compounds are those where A and B have the abovementioned meanings and Ar is β-naphthyl which is substituted by 1 or 2 methoxy groups in position 4, 5, 6, 7 and/or 8 or by a methylenedioxy or ethylenedioxy group in these positions.

The novel compounds have one or two asymmetric centers. They may be in the form either of the racemates or of the antipodes with respect to the two asymmetric centers. Compounds which have the R configuration and the phenylalanine moiety are preferred.

The novel compounds can, if required, be in the form of their salts with physiologically tolerated acids. Examples of suitable physiologically tolerated acids are: hydrochloric acid, hydroiodic acid, sulfuric acid, phosphoric acid, acetic acid, citric acid, malonic acid, salicylic acid, maleic acid, fumaric acid, succinic acid, ascorbic acid, malic acid, methanesulfonic acid, lactic acid, gluconic acid, glucuronic acid, sulfamic acid, benzoic acid and tartaric acid.

The novel compounds are prepared by reacting a compound of the formula II

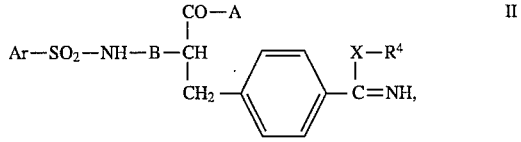

where R⁴ is $C_{1-3}$-alkyl or benzyl and X is oxygen or sulfur, with ammonia or an ammonium salt, and converting the resulting compounds where appropriate into their salts with physiologically tolerated acids.

The reaction of II is normally carried out at 40° to 80° C. in a polar organic solvent such as tetrahydrofuran, acetone, dioxane, methanol or dimethylformamide. It is usually complete after 1 to 10 hours.

The starting materials required for the preparation of the novel compounds have not previously been described. They can be obtained as follows:

I Synthesis of the p-cyanophenylalanine moiety a) The preparation of p-cyanophenylalanine is described in DD-C 155 954. After alkylation of acetaminomalonic ester with p-cyanobenzyl halides, the resulting adduct is converted by hydrolysis and decarboxylation into p-cyanophenylalanine, although partial hydrolysis of the nitrile functionality results in by-products which are difficult to remove. The processes described below provide the required p-cyanophenylalanine in higher purity and yield.

b) p-Cyanophenylalanine is prepared by reacting isocyanoacetic ester with secondary amines $HNR^1R^2$ to give the compounds 2 where $R^1$ and $R^2$ have the stated meanings (see synthesis 1977, 249).

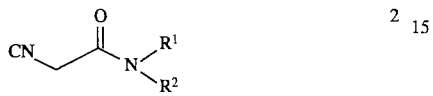

These compounds ($R^1 \neq H$, $R^2 \neq H$) are then deprotonated with suitable bases (eg. potassium tertbutylate, butyllithium or lithium diisopropylamide) and reacted with p-cyanobenzyl compounds of the type 3. X in these is a nucleofugic group such as halogen or alkyl- or arylsulfonate. In contrast to the reaction of isocyanoacetic esters with p-cyanobenzyl halides there is almost exclusively monoalkylation with the isocyanoacetamides 2.

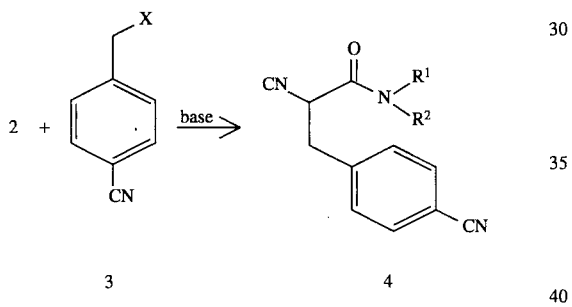

Subsequently, the isocyanide group in 4 is hydrolyzed in aqueous acid to give the amine 5.

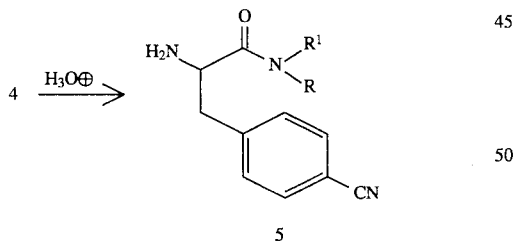

c) The reaction of N-(diphenylmethylene)glycine ester ($R^4 = C_1 - C_6$) 6 with p-cyanobenzyl compounds 3 using suitable bases yields the monoalkylated product 7 whose protective group is hydrolyzed under acid conditions (see J. Org. Chem. 47, (1982) 2663–2666). Use of benzaldehyde imines in place of the benzophenone imines with p-cyanobenzyl bromide results in a mixture of mono- and dialkylated product.

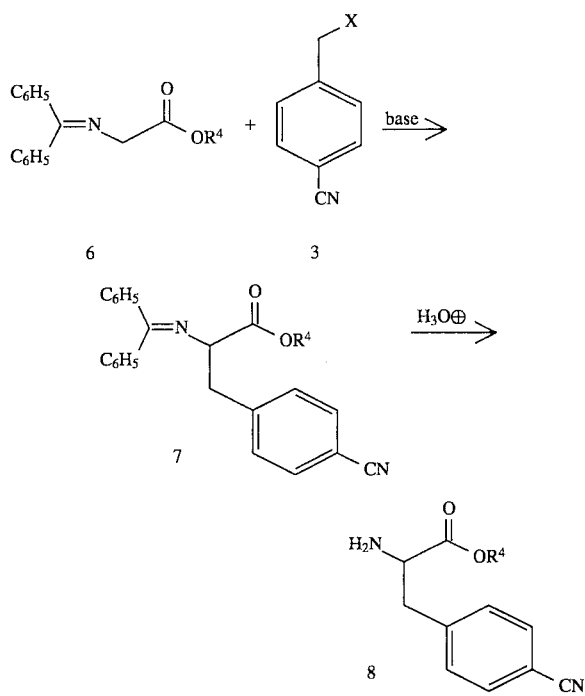

d) The enantiomerically pure amines 5 and 8 can be obtained by racemate resolution with optically active acids or by enantioselective syntheses as in e) or f).

e) Reaction of the bislactim ether 9 ($R^5 = C_1 - C_4$) with p-cyanobenzyl compounds 3 by methods known from the literature (Angew. Chem. 92, (1980) 205; Synthesis 1982, 864, 868; Tetrahedron 39 (1983) 2085, Ann. Chem. 1983, 1133) yields the compounds 10. Acid hydrolysis of these substances provides the enantiomerically pure p-cyanophenylalanine ester 11. In this case there is formation of the alanine ester 11 with the S configuration from the lactim ethers 9 with the R configuration, and vice versa, and it is preferable to employ the compounds 9 with the S configuration.

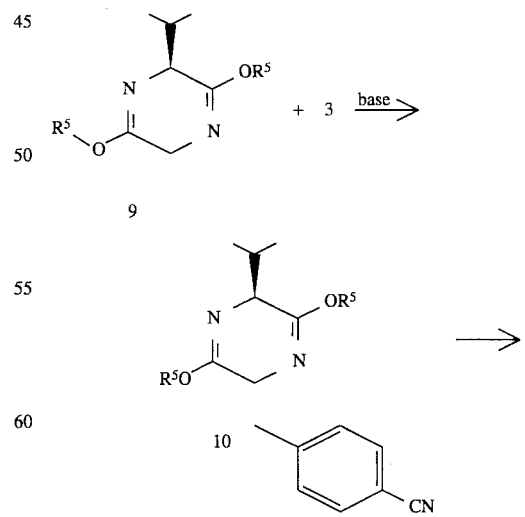

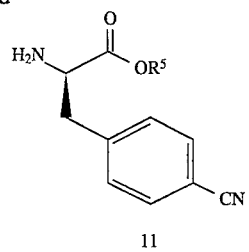

11

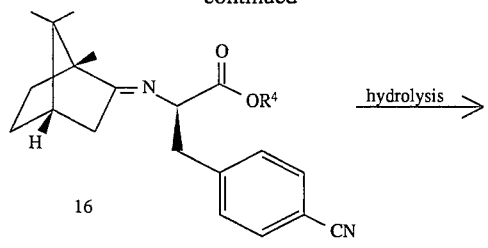

16

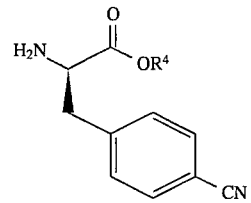

17 f) Reaction of imidazolidinones 12 with p-cyanobenzyl compounds 3 in a similar manner to the methods disclosed in the literature (Tetrahedron 44 (1988) 5277) results, after hydrolysis of the intermediates 13, in the p-cyanophenylalanine 14.

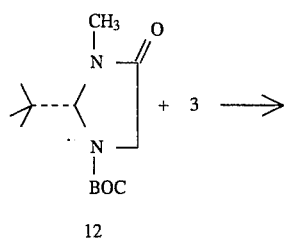

12

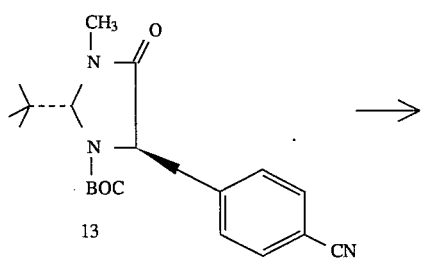

13

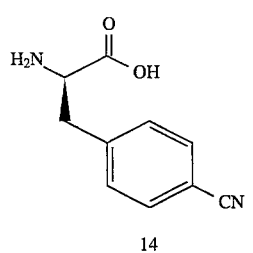

14 g) When chiral ketimine derivatives are used in method c), eg. camphor ketimine derivative 15, the chiral alanine esters 17 result (see Synth. Comm. 19 (1983) 881–888).

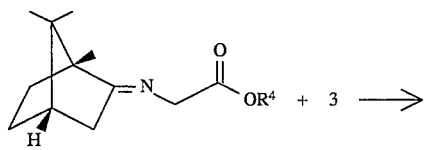

15 h) Temporary protection of the amino group in p-cyanophenylalanine ester 8, 11 or 17 makes it possible, after ester hydrolysis and activation of the carboxylic acid, to prepare other esters by reaction with alcohols, as well as to obtain the corresponding amides 21 by reaction with ammonia or primary or secondary amines, where $R^1$ and $R^2$ can also be H. The compounds 18 to 21 can be either racemic or enantiomerically pure.

Chemical methods for forming amide linkages are described in detail in Müller, Methoden der Organischen Chemie Vol. XV/2, pp. 1–364, Thieme Verlag, Stuttgart, 1974; Bodanszky, Klausher, Ondetti, Peptide Synthesis, pp. 85–128, John Wiley & Sons, New York, 1976 and other standard works of peptide chemistry. Particularly preferred methods are the azide method, the symmetrical and mixed anhydride method, active esters generated in situ or preformed, and the formation of amide linkages using coupling reagents (activators), especially dicyclohexylcarbodiimide (DCC), diisopropylcarbodiimide (DIC), 1-ethoxycarbonyl-2-ethoxy-1,2-dihydroquinoline (EEDQ), 1-ethyl-3-(3-dimethylaminopropyl)carbodiimide hydrochloride (EDCI), n-propanephosphonic anhydride (PPA), bis (2-oxo-3-oxazolidinyl)phosphinic chloride (BOP-Cl), diphenylphosphoryl azide (DPPA), Castro's reagent (BOP), O-benzotriazolyl-N,N,N',N'-tetramethyluronium salts (HBTU), 2,5-diphenyl-2,3-dihydro-3-oxo-4-hydroxythiophene dioxide (Steglichs Reagenz; HOTDO) and 1,1'-carbonyldiimidazole (CDI). The coupling reagents can be employed alone or in combination with additives such as 4-dimethylaminopyridine (DMAP), N-hydroxybenzotriazole (HOBt), N-hydroxybenzotriazine (HOOBt), N-hydroxysuccinimide (HOSu) or 2-hydroxypyridine.

Three protective group techniques which are known from the literature are preferred for the peptide syntheses: the benzyloxycarbonyl (Z), the t-butyloxycarbonyl (Boc) and the 9-fluorenylmethyloxycarbonyl (Fmoc) protective group techniques.

8,11,17 $\xrightarrow{\text{Protective group}}$

-continued

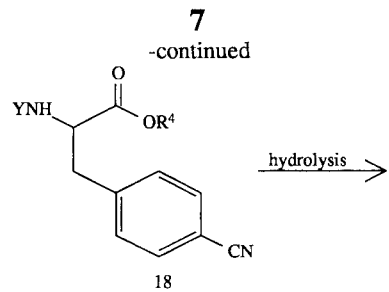
18

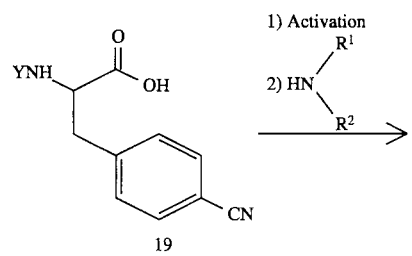
19

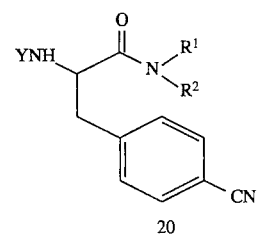
20

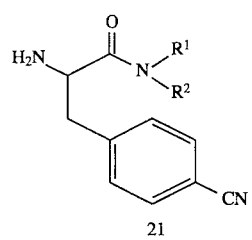
21

II Synthesis of the pyrrolidinones a) Methionine derivatives as precursors

The amines 5, 8, 11, 17 and 21, which are called only 22 ($R^3 \neq H$, A as in formula I) for simplicity hereinafter, are reacted under the conditions customary in peptide chemistry (see above) with N-protected methionine 23 to 24. Y is Z, Boc or Fmoc.

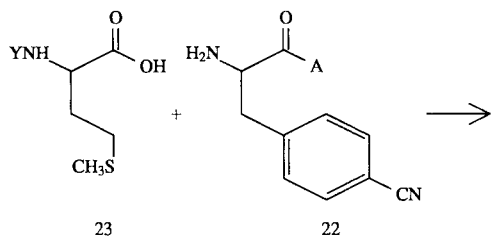

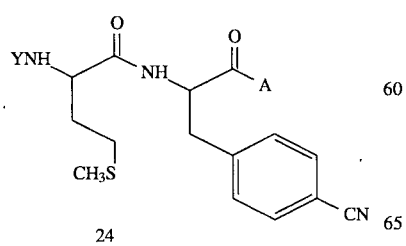
24

The sulfonium salt 25 which is obtained by alkylation of 24 with an alkyl or aralkyl halide R'X, preferably methyl iodide or benzyl bromide, can be cyclized with suitable bases to give the pyrrolidinone ring 26. Suitable bases are sodium hydride, potassium tert-butylate, butyllithium, lithium bis(trimethylsilyl)amide and lithium diisopropylamide, the latter being preferred. Elimination of the protective group yields the amine 27.

24 + R'X ⟶

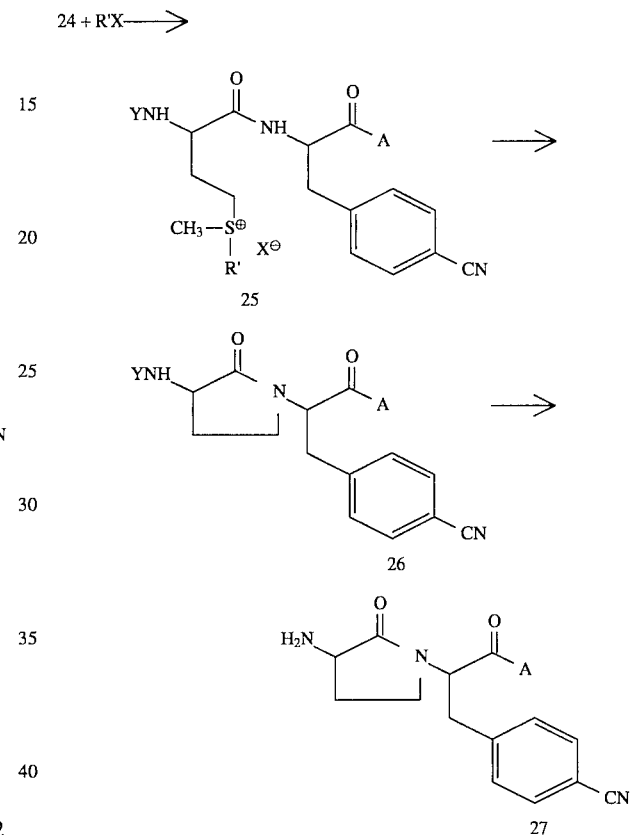

b) Aspartic acid derivatives as precursors

Reaction of the N-protected aspartic acid derivatives 28 ($R^5 = C_1$–$C_4$-alkyl, benzyl) with the amine 5 or 21 under the conditions customary in peptide chemistry (see above) yields the intermediate 29 whose ester moiety is selectively reduced to the alcohol and converted into a leaving group X (eg. halogen, mesylate, triflate, tosylate). Treatment with suitable bases (similar to methionine, see above) results in the pyrrolidinones 32, which are subsequently deprotected.

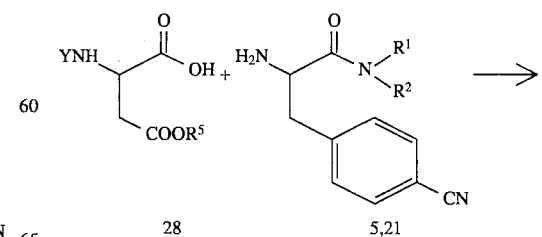
28        5,21

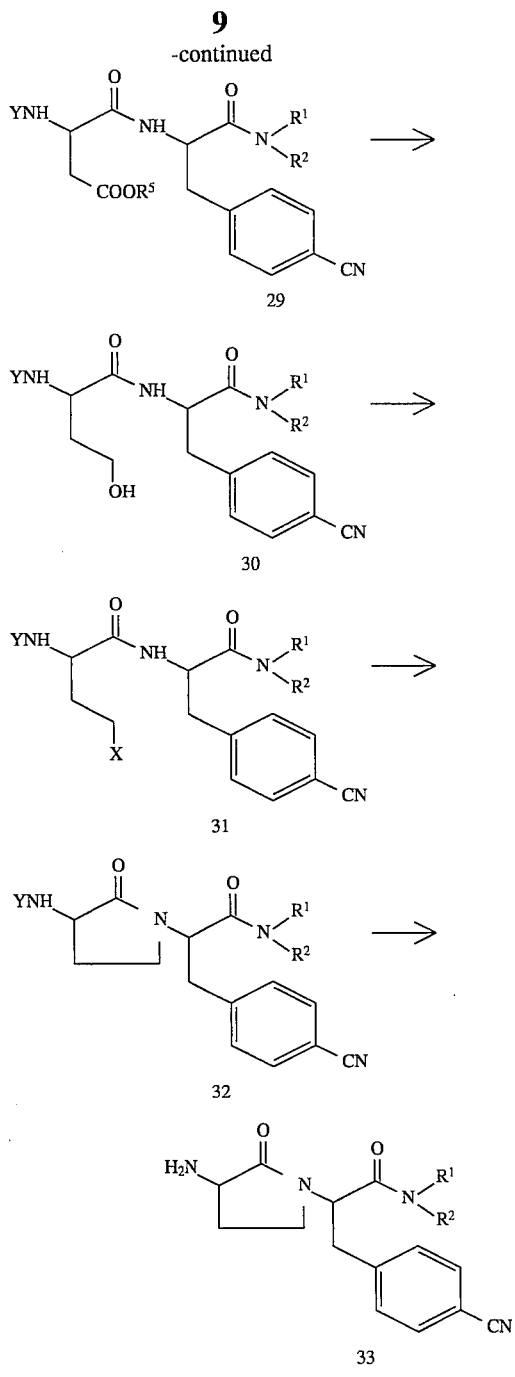

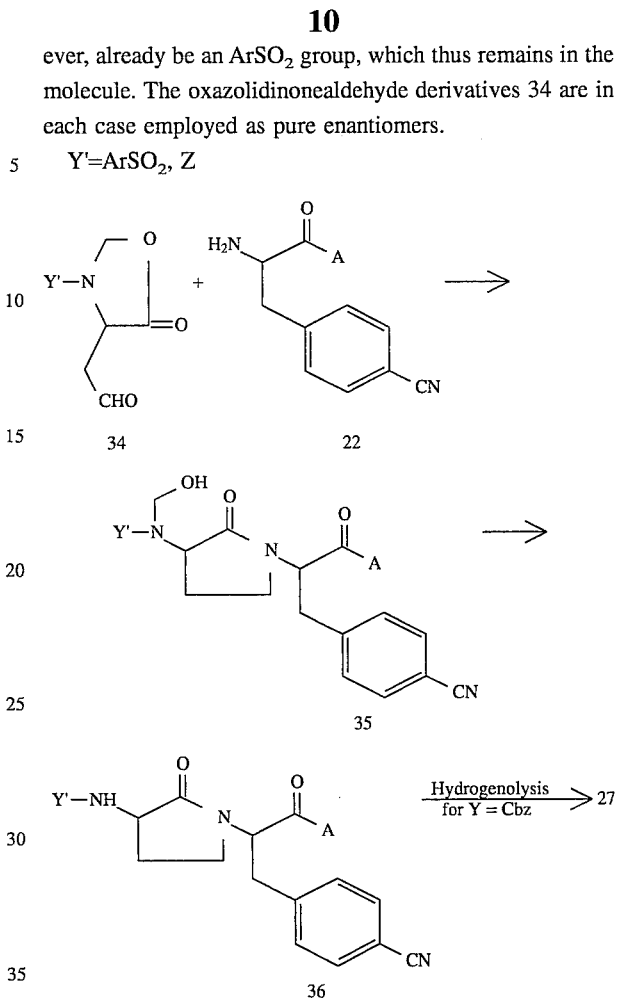

c) Oxazolidinonealdehyde derivatives as precursors

Reaction of protected derivatives 34 whose synthesis is described for Y'=Z (TH 42 (1986) 6551) with the amines 22 (R³≠H) under reductive conditions yields the compounds 35, which are converted with bases into the protected pyrrolidinones 36. When Z is used as protective group, this is subsequently eliminated by hydrogenolysis. Y' can, how- ever, already be an ArSO₂ group, which thus remains in the molecule. The oxazolidinonealdehyde derivatives 34 are in each case employed as pure enantiomers.

Y'=ArSO₂, Z

III Synthesis of the piperidinones a) Glutamic acid derivatives as precursors

Similar to the preparation of the pyrrolidinones 33 starting from the N-protected aspartic acid derivative 28 it is possible to prepare the corresponding piperidinones 39 when the homologous glutamic acid derivative 37 is employed as precursor.

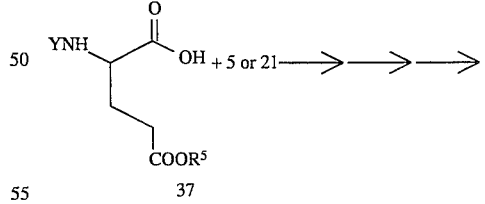

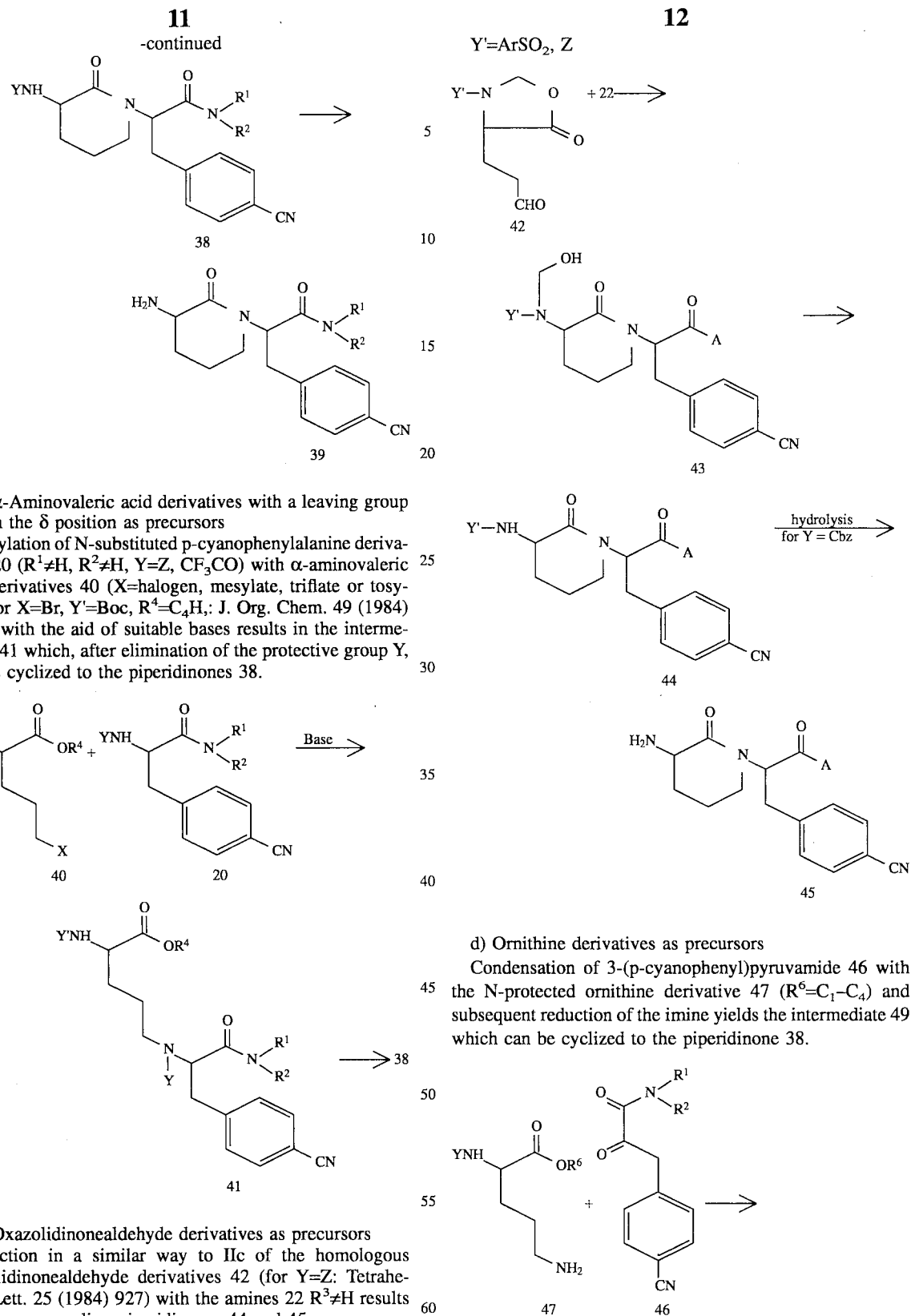

b) α-Aminovaleric acid derivatives with a leaving group in the δ position as precursors Alkylation of N-substituted p-cyanophenylalanine derivatives 20 ($R^1 \neq H$, $R^2 \neq H$, Y=Z, $CF_3CO$) with α-aminovaleric acid derivatives 40 (X=halogen, mesylate, triflate or tosylate; for X=Br, Y'=Boc, $R^4=C_4H_9$: J. Org. Chem. 49 (1984) 3527) with the aid of suitable bases results in the intermediates 41 which, after elimination of the protective group Y, can be cyclized to the piperidinones 38.

c) Oxazolidinonealdehyde derivatives as precursors

Reaction in a similar way to IIc of the homologous oxazolidinonealdehyde derivatives 42 (for Y=Z: Tetrahedron Lett. 25 (1984) 927) with the amines 22 $R^3 \neq H$ results in the corresponding piperidinones 44 and 45.

If Y' is $ArSO_2$, this group remains in the molecule.

d) Ornithine derivatives as precursors

Condensation of 3-(p-cyanophenyl)pyruvamide 46 with the N-protected ornithine derivative 47 ($R^6=C_1-C_4$) and subsequent reduction of the imine yields the intermediate 49 which can be cyclized to the piperidinone 38.

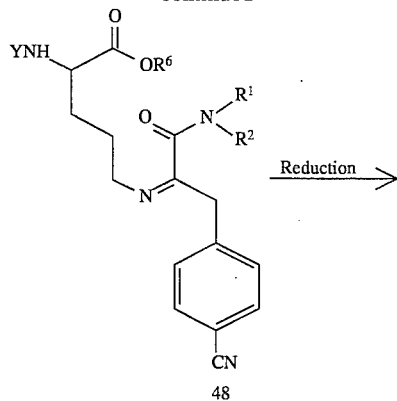

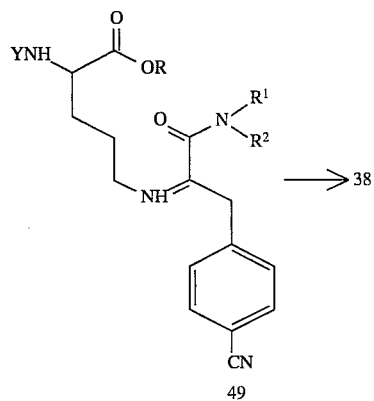

e) Isocyanoacetic ester as precursor

Similar to the reaction of isocyanoacetic ester with piperidine (Ib), reaction with the amine 5 or 21 (R$^1$≠H, R$^2$≠H) yields the intermediate 51, which can be cyclized with 1,3-dihaloalkanes (X$^1$, X$^2$=Hal) in the presence of bases to give the piperidinone 52. The isocyanide can be converted by hydrolysis with aqueous acid into the amine 39.

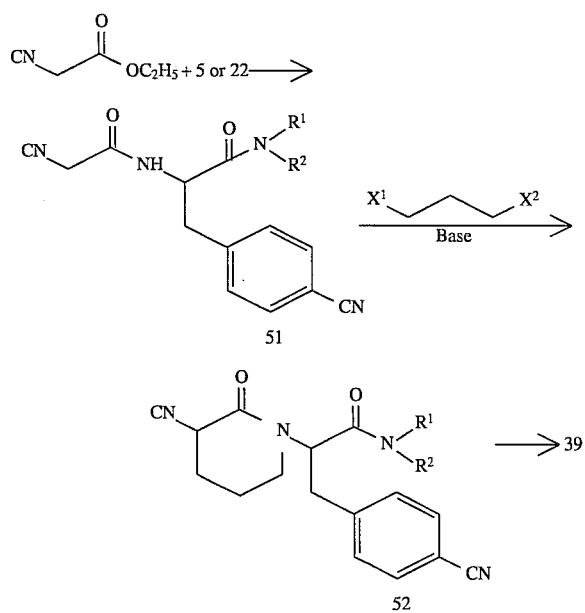

IV Reaction of the pyrrolidones and piperidinones with aromatic sulfonyl chlorides The intermediates 27, 33, 39 and 45 can be reacted with the aromatic sulfonyl chlorides ArSO$_2$Cl with base catalysis to give the sulfonamides 53 and 54.

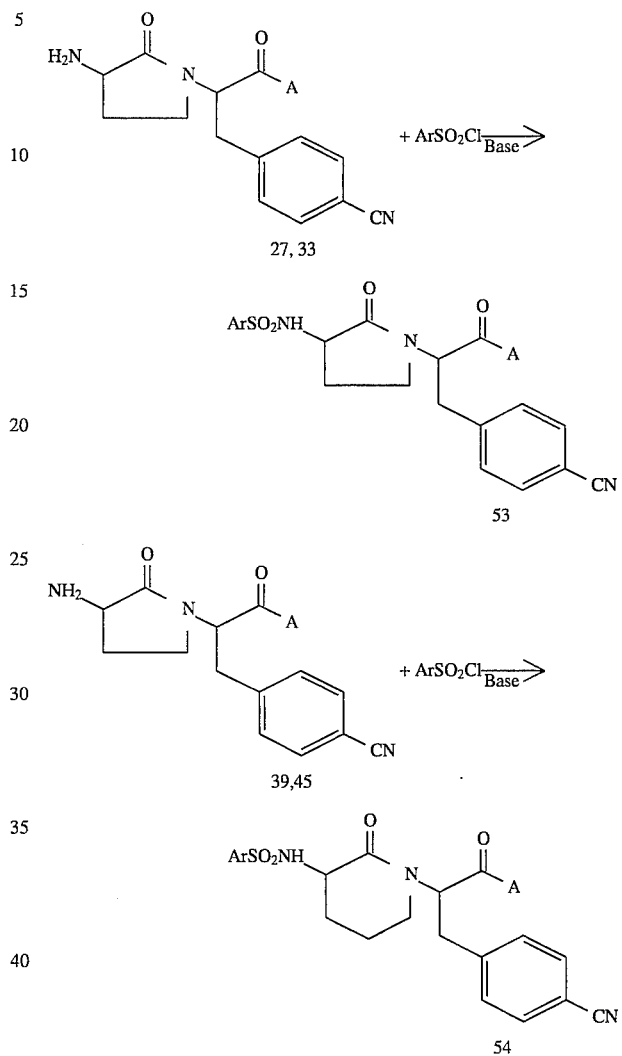

V Synthesis of the pyridones

N-alkylation of 3-nitro-2-hydroxypyridine 55 with α-haloacetic esters (R$^4$=C$_1$–C$_6$, X=Cl, Br) 56 results in the pyridones 57. The tert-butylesters (R$^4$=C(CH$_3$)$_3$) can easily be cleaved with trifluoroacetic acid. The carboxylic acid 58 is activated and then reacted with the amines HNR$^1$R$^2$ (R$^1$, R$^2$≠H) to give the intermediates 59. The latter can also be prepared directly by reacting 55 with α-haloacetamides (R$^1$, R$^2$≠H, X=Cl, Br) 60. Catalytic reduction of the nitro group in 59 yields the aminopyridones 61. The latter are reacted with the aromatic sulfonyl chlorides ArSO$_2$Cl, and subsequently the SO$_2$NH group is protected for the subsequent alkylation with di-tert-butyl dicarbonate to give the intermediates 63. 63 is deprotonated (preferably with lithium diisopropylamide) and then alkylated with p-cyanobenzyl halide 3 to give the pyridone 64. The Boc protective group can be eliminated subsequently or after conversion of the cyano into the amidino group (see section VII) with trifluoroacetic acid.

It is furthermore possible to convert the ester 57

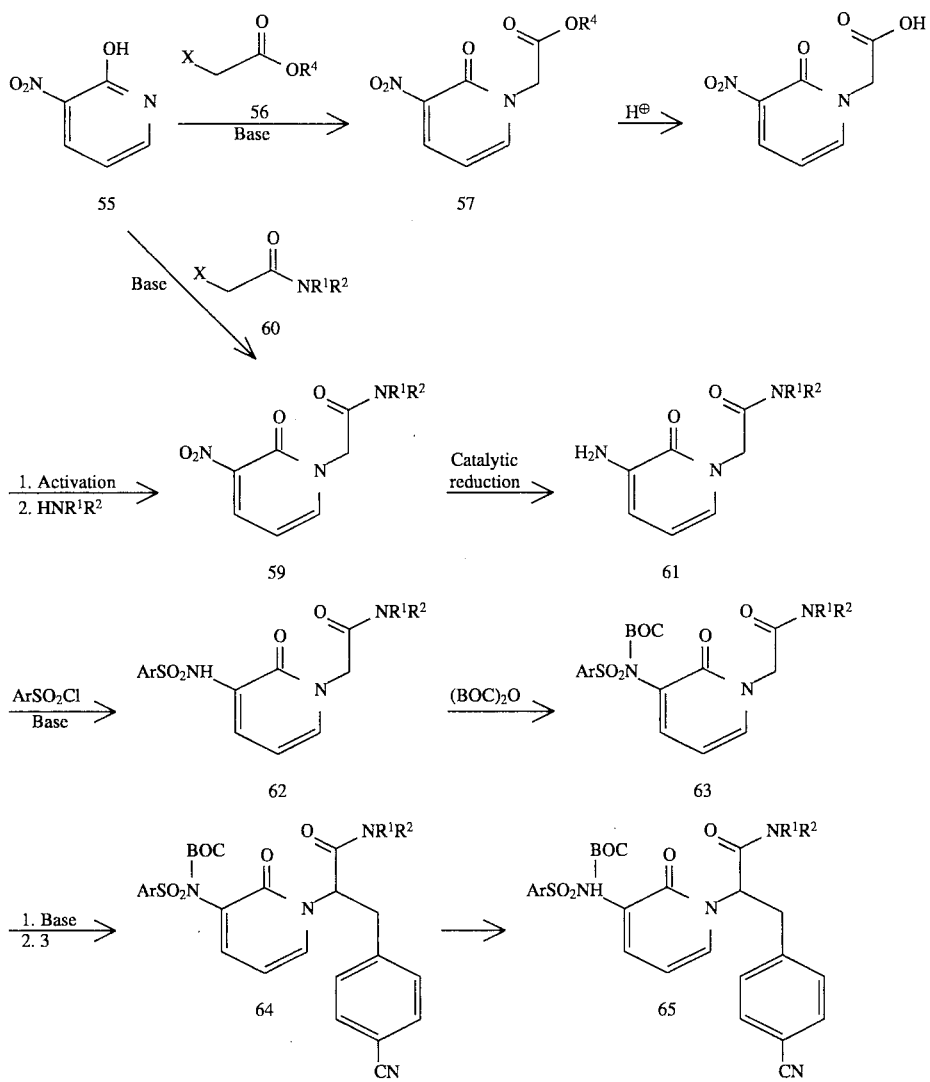

into the ester 66 or 67 in a similar way:

57 →→→→→

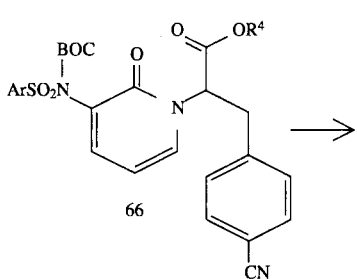

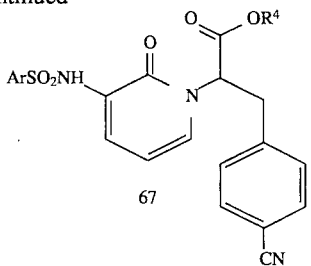

VI Conversion of the ester moieties in the intermediates 26, 36, 44, 53, 54, 66 and 67.

In a similar way to Ih, the ester moieties in 26, 36, 44, 53 and 54 (A=OR$^3$R$^3$≠H→R$^3$=H) or 66 and 67 (R$^4$≠H, →R$^4$=H), can hydrolyzed, and the carboxylic acids can be activated and subsequently reacted with alcohols to give other esters (A=OR$^3$) and, by reaction with amines (HNR$^1$R$^2$), the corresponding amides (A=NR$^1$R$^2$).

VII conversion of the cyano group into the amidino group

One way of converting the cyano group in 53, 54, 65 and 67 is typically via the Pinner reaction by acid-catalyzed addition of alcohols (R$^7$=C$_1$–C$_4$) to form the imino ethers 68, which with ammonia or ammonium salts form the corresponding amidines I. Another way is to produce the amidino group in I by addition of hydrogen sulfide onto the cyano group in 53, 54, 64, 65, 66 or 67, alkylation on the sulfur of the thioamides 69 or 70 with alkyl halides (X=Hal, $R^8=C_1-C_3$ alkyl, benzyl) and reaction of the imino thioethers 71 or 72 with ammonia or ammonium salts. The Boc-protected amidine derivatives can, after elimination of the protective group (preferably with trifluoroacetic acid in methylene chloride), be converted into the final products I.

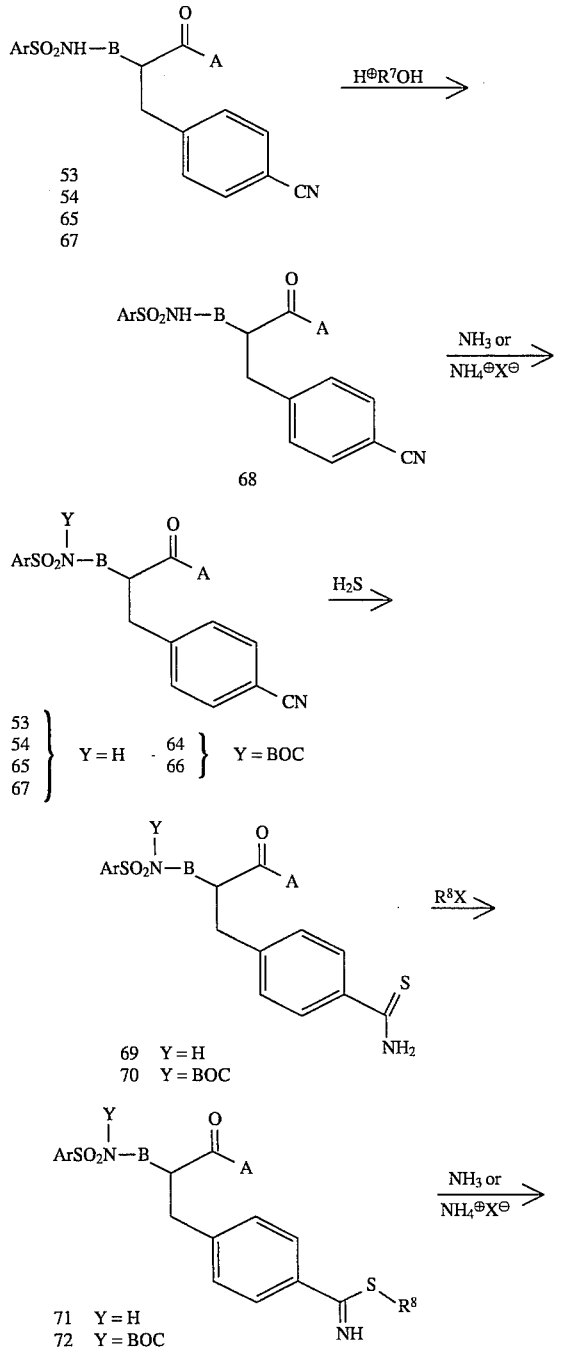

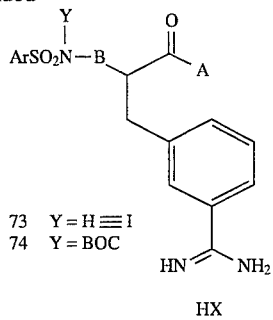

73 Y = H ≡ I
74 Y = BOC

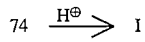

The compounds according to the invention have a good thrombin-inhibitory action essentially without any affect on other serine proteases (eg. trypsin and plasmin). They can therefore be used for the prophylaxis and therapy of thromboembolic disorders such as myocardial infarct, thromboses and embolisms.

The pharmacological characterization of the novel compounds as thrombin inhibitors was carried out using the following test systems:

1. Plasma thrombin time in vitro

Citrated plasma is obtained by mixing human blood with sodium citrate (0.11 mol/l) (9 parts of blood+ 1 part of sodium citrate) and subsequently centrifuging at 1600 xg for 10 min at room temperature. 50 µl of citrate plasma are added to 50 µl of the test substance solution or solvent and incubated at 37° C. for 2 min. Then 100 µl of thrombin reagent equilibrated at 37° C. (Boehringer Mannheim) are pipetted in, and the time until coagulation occurs is measured in a photometric coagulometer.

The concentration of a test substance in mol/l which increases the plasma thrombin time by 100% is calculated as the $EC_{100}$, which is a measure of the relative efficacy.

The plasma thrombin time registers the thrombin-induced fibrin formation from fibrinogen and the aggregation of fibrin, ie. the last step in coagulation.

2. Amidolytic determination of the activity of thrombin and other serine proteases (trypsin, chymotrypsin, plasmin, factor Xa, active protein C)

Test principle:

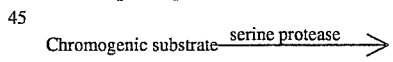

peptide + p-nitroaniline (yellow)

250 µl of thrombin (0.124 IU/ml, FC 0.1 IU/ml) in tris buffer (tris 50 mmol/l, NaCl 154 mmol/l, pH 8.0) are introduced into each well of microtiter plates. This solution is mixed with 10 µl of solvent (control) or test substance and, after mixing for 1 min, incubated at 25° C. for 4 min. The reaction is then started by adding 50 µl of substrate solution (S-2238, 0.62 mmol/l, FC 0.1 mmol/l) and, after brief mixing, incubated at 25° C. After 5 min, the reaction is stopped by adding 50 µl of 35% strength acetic acid, and the extinction at 405 run is measured (versus 630 run). The extinction measured after the end of the reaction is proportional to the enzyme activity.

The concentration of a test substance in mol/l which reduces the enzyme activity by 50% is calculated as the $IC_{50}$, which is a measure of the relative efficacy.

The effect on the amidolytic activity of other serine proteases is also investigated in a similar way to thrombin:

| | |
|---|---|
| Trypsin (0.1 mg/l) | with S-2222 (0.1 mmol/l) |
| Chymotrypsin (0.2 mg/l) | with S-2586 (0.1 mmol/l) |
| Plasmin (0.04 CU/ml) | with S-2251 (0.1 mmol/l) |
| Factor Xa (0.2 nkat/ml) | with S-2765 (0.1 mmol/l) |
| Active protein C | with S-2366 (0.2 mmol/l) |

(in each case the final concentration in the test). The results of these tests provide information about the selectivity of the action of test substances.

3. Thrombin-induced platelet aggregation in vitro

Fresh human citrated blood (9 parts of blood+1 part of sodium citrate 0.11 mol/l) is centrifuged at 250 xg for 16 min and at 3670 xg for 20 min to obtain platelet-rich plasma (PRP) and platelet-poor plasma (PPP) respectively.

Platelet aggregation is determined by adding 5 μl of solvent (control) or test substance to 445 μl of PRP and incubating at room temperature for 5 min. The mixture is then incubated in an aggregometer (ELVI 840) at 37° C. for 3 min and stirred at 1000 rpm for 4 min. Aggregation is started by adding 50 μl of thrombin solution (final concentration in the mixture: 0.15 IU/ml). The platelet aggregation is determined from the change in the transmission of the sample per unit time (slope method).

The concentration of a test substance in mol/l which inhibits platelet aggregation by 50% is calculated as the $IC_{50}$, which is a measure of the relative activity.

4. Antithrombotic action in an arteriovenous shunt in rats

In this experiment, thrombosis is induced by a glass capillary in an arteriovenous shunt.

The anesthetized (urethane 25%, 2×8 mg/kg i.p.) rat is fixed supine on a stage equilibrated at 37° C. The right carotid artery and jugular vein are exposed and short polyethylene catheters (Portex, PE 50) are implanted, then filled with physiological NaCl solution and closed with clips. The free ends of the catheters are connected by a glass capillary (internal diameter 1.0 mm, length 20.0 mm) which acts as thrombogenic surface.

The test substance can be administered i.v., s.c., orally or as infusion. After the required incubation time (5, 60 or 360 min) with the test substance or solvent (control), the shunt is opened by removing the clips. The flow of blood through the shunt leads to a rapid rise in the temperature, which is measured at the middle of the glass capillary. The increase from room temperature to body temperature is an indicator of the patency of the shunt. The temperature is recorded continuously until the shunt becomes blocked, but for not longer than 30 min.

Additional blood samples are taken when the shunt is opened and at the end of the experiment to determine the anti-FIIa activity in the plasma.

The results of the experiment are analyzed by a linear regression calculation on the value for the log dose and the time (difference between the blockage times in the treated group and control group). The equation of the regression line is used to calculate the ED 15 min (the dose which increases the blockage time by 15 min compared with the control group) to compare the activity of different test substances.

The novel compounds show very good properties in these tests.

The novel compounds can be administered in a conventional way orally or parenterally (subcutaneously, intravenously, intramuscularly, intraperitoneally). Administration can also take place with vapors or sprays through the nasopharyngeal space.

The dosage depends on the age, condition and weight of the patient and on the mode of administration. The daily dose of active substance is, as a rule, about 10–1000 mg/kg of body weight on oral administration and about 1–100 mg/kg of bodyweight on parenteral administration.

The novel compounds can be used in the conventional solid or liquid pharmaceutical forms, eg. as uncoated or (film-)coated tablets, capsules, powders, granules, suppositories, solutions, ointments, creams or sprays. These are produced in a conventional way. The active substances can for this purpose be processed with conventional pharmaceutical aids such as tablet binders, fillers, preservatives, tablet disintegrants, flow regulators, plasticizers, wetting agents, dispersants, emulsifiers, solvents, retardants, antioxidants and/or propellant gases (cf. H. Sucker et al.: Pharmazeutische Technologie, Thieme-Verlag, Stuttgart, 1978). The administration forms obtained in this way normally contain from 1 to 99 percent by weight of active substance.

EXPERIMENTAL SECTION

All the reactions were carried out under inert gas, preferably nitrogen.

The solvents used for the reactions were dried over molecular sieves.

EXAMPLE 1 a) Preparation of N-isocyanoacetylpiperidine 48.7 g (570 mmol) of dry piperidine were added to 25.8 g (228 mmol) of ethyl isocyanoacetate in 200 ml of dry methanol, and the mixture was stirred at room temperature overnight. It was subsequently evaporated to dryness and crystallized from ether/isopropanol to give 33 g (=95% of theory) of pure N-isocyanoacetylpiperidine as beige solid.

b) Preparation of 3-(p-cyanophenyl)-2-isocyanopropionylpiperidine 22.0 g (144.5 mmol) of N-isocyanoacetylpiperidine in 160 ml of THF were added dropwise to 159 mmol of lithium diisopropylamide in 430 ml of THF at –70° C. Subsequently 28.3 g (144.5 mmol) of p-cyanobenzyl bromide dissolved in 300 ml of THF were added dropwise to the mixture at –70° C. and, after stirring at this temperature for 3 h (reaction complete according to TLC, mobile phase $CH_2Cl_2/CH_3OH$ 9/1), 70 ml of water were added dropwise. The solution was concentrated under reduced pressure, the residue was acidified with 1N HCl and extracted with methylene chloride, and the organic phase was dried over magnesium sulfate and evaporated. The solid product was mixed with ether, stirred overnight and filtered off with suction. 30.9 g (plus 3.3 g by working up the mother liquor) of 3-(p-cyanophenyl)-2-isocyanopropionylpiperidine were obtained as a white solid (86% of theory).

c) Preparation of p-cyanophenylalaninylpiperidine hydrochloride 17.4 g (59.2 mmol) of 3-(p-cyanophenyl)-2-isocyanopropionylpiperidine were stirred together with 160 ml of dioxane and 24 ml of concentrated hydrochloric acid at 60° C. for 45–60 min (TLC monitoring, mobile phase $CH_2Cl_2/CH_3OH$ 9/1), and then the mixture was concentrated under reduced pressure, the residue was taken up in water, the aqueous phase was extracted with a little ethyl acetate, mixed with ammonia and extracted with methylene chloride, and the organic phase was dried over magnesium sulfate and concentrated under reduced pressure. The residue was taken up in acetone, and the hydrochloride was precipitated with hydrochloric acid in ether. The precipitate was filtered off with suction and washed with ether to give 16.3 g (≈83%) of p-cyanophenylalaninylpiperidine hydrochloride as white solid.

d) Preparation of Boc-L-(S-methyl)methionyl-D,L-4-cyanophenylalaninylpiperidine iodide 11.2 g (22.92 mmol) of Boc-L-methionyl-D,L-4-cyanophenylalaninylpiperidine were stirred together with 35 ml of methylene chloride and 45 ml of methyl iodide in a closed flask at room temperature for 4 days. Methylene chloride and excess methyl iodide were removed initially under water pump vacuum and subsequently under high vacuum at room temperature. The residue was used without further purification for the cyclization described below under e).

e) Preparation of 3-(tert-butyloxycarbonylamino)-1-[2-(4-cyanophenyl)-1-piperidinocarbonylethyl]-2-pyrrolidinone The product prepared as described in d) above was dissolved in 100 ml of THF and added dropwise to a solution of 65.9 mmol of lithium diisopropylamide in 300 ml of THF prepared at −70° C. After 30 min at −70° C., the mixture was allowed to warm slowly to room temperature and was stirred at this temperature overnight. The mixture was then concentrated under reduced pressure, the residue was taken up in ether, the solution was washed with 1N hydrochloric acid, the fraction insoluble in ether was removed by filtration, and the ether phase was washed with water, dried over magnesium sulfate and concentrated under reduced pressure to give 8.7 g (≈86%) of slightly impure 3-(tert-butyloxycarbonylamino)- 1-[2-(4-cyanophenyl)-1-piperidinocarbonylethyl]- 2-pyrrolidinone, which was used without further purification.

f) Preparation of 3-amino-1-[2-(4-cyanophenyl)-1-piperidinocarbonylethyl]-2-pyrrolidinone (as trifluoroacetate)

The crude product obtained as in e) was stirred together with 43 ml of methylene chloride and 23 ml of trifluoroacetic acid at room temperature for 90 min. The mixture was then concentrated initially under water pump vacuum and then under high vacuum at room temperature. The resulting slightly impure 3-amino-1-[2-(4-cyanophenyl)-1-piperidinocarbonylethyl] -2-pyrrolidinone (as trifluoroacetate) was used without further purification in the next stage.

g) Preparation of 3-(6,7-dimethoxynaphthalene-2-sulfonylamino)-1-[2-(4-cyanophenyl)-1-piperidinocarbonylethyl] -2-pyrrolidinone The product obtained as in f) was dissolved in 25 ml of methylene chloride, and 5.67 g (19.8 mmol) of 6,7-dimethoxynaphthalene-2-sulfonyl chloride dissolved in 25 ml of methylene chloride were added. Subsequently, 7.6 ml of triethylamine were added, and the mixture was stirred at room temperature overnight and then concentrated under reduced pressure. The residue was taken up in ethyl acetate, and the solution was extracted with 2N hydrochloric acid and subsequently with saturated brine, dried over magnesium sulfate and concentrated. The mixture was purified by column chromatography (250 ml of silica gel 0.063–0.200 nun, methylene chloride with methanol increasing from 0 to 3%). 7.75 g of almost pure 3-(6,7-dimethyoxynaphthalene-2-sulfonylamino)- 1-[2-(4-cyanophenyl)-1-piperidinocarbonylethyl]- 2-pyrrolidinone (yield over two stages 66%) were obtained.

h) Preparation of 3-(6,7-dimethoxynaphthalene-2-sulfonylamino)-1-[2-(4-aminothiocarbonylphenyl)-1-piperidinocarbonylethyl)-2-pyrrolidinone 4.6 g (7.78 mmol) of 3-(6,7-dimethoxynaphthalene-2-sulfonylamino)-1-[2-(4-cyanophenyl)-1-piperidinocarbonylethyl]- 2-pyrrolidinone were dissolved in 5 ml of triethylamine and 80 ml of pyridine, and hydrogen sulfide was passed into saturation. The mixture was left to stand overnight and subsequently added dropwise to a mixture of 600 g of ice and 100 ml of concentrated hydrochloric acid. The precipitate was filtered off with suction and dissolved in THF, and the solution was dried over magnesium sulfate and concentrated. The residue was mixed with ether and, after stirring at room temperature for 30 min, the precipitate was filtered off with suction. The slightly impure 3-(6,7-dimethoxynaphthalene-2-sulfonylamino)- 1-[2-(4-aminothiocarbonylphenyl)-1-piperidinocarbonylethyl] -2-pyrrolidinone was used without further purification in the next stage.

i) Preparation of 3-(6,7-dimethoxynaphthalene-2-sulfonylamino)-1-[2-(4-methylthio(imino)methylphenyl)-1-piperidinocarbonylethyl]-2-pyrrolidinone The crude product obtained as in h) was mixed with 10 ml of methyl iodide and stirred at room temperature for 75 min. The mixture was then evaporated to dryness, initially under water pump vacuum and then under high vacuum at room temperature. The slightly impure 3-(6,7-dimethoxynaphthalene-2-sulfonylamino)- 1-[2-(4-methylthio(imino)methylphenyl)-1-piperidinocarbonylethyl] -2-pyrrolidinone was used without purification in the next stage.

j) Preparation of 3-(6,7-dimethoxynaphthalene-2-sulfonylamino)-1-[2-(4-amidinophenyl)-1-piperidinocarbonylethyl]-2-pyrrolidinone hydroiodide The crude product obtained as in i) was stirred together with 1.28 g of ammonium acetate and 80 ml of methanol at 60°–65° C. for 90 min and subsequently concentrated under reduced pressure. The residue was taken up in 80 ml of methylene chloride, and insolubles were removed by filtration. The filtrate was concentrated under reduced pressure. The residue was taken up in a little ethanol, and the product was precipitated with ethyl acetate. This purification procedure was repeated several times. The collected mother liquors could also be purified in this way. 2.9 g (≈50.6% over 3 stages) of pure 3-(6,7-dimethoxynaphthalene-2-sulfonylamino)- 1-[2-(4-amidinophenyl)-1-piperidinocarbonylethyl]- 2-pyrrolidinone hydroiodide were obtained as a white solid.

The mixture of (3S)-(6,7-dimethoxynaphthalene- 2-sulfonylamino)-1-[2(R, S)-(4-amidinophenyl)- 1-piperidinocarbonylethyl]-2-pyrrolidinone diastereomers could be separated by MPLC.

The 6,7-dimethoxynaphthalene-2-sulfonyl chloride required for reaction g) was prepared as follows:

9.6 g of 50% sodium hydride suspension (200 mmol) were treated with hexane to remove oil, and about 250 ml of DMF were added. To this was added dropwise a solution of 14.4 g of sodium 6,7-dihydroxynaphthalene-2-sulfonate (55 mmol) in 200 ml of DMF at room temperature, and reaction was allowed to continue for 45 min after the evolution of hydrogen ceased. Subsequently 51.1 g (360 mmol) of methyl iodide were added dropwise over the course of 20 min, during which the temperature did not exceed 25° C., and the mixture was stirred at room temperature overnight and subsequently introduced into a little ice-water, and the mixture was then concentrated under reduced pressure and taken up in acetone and concentrated several times. The residue was recrystallized from 1 l of acetone.

The resulting crude sodium 6,7-dimethoxynaphthalene-2-sulfonate, which still contained some inorganic salt, was without further purification stirred together with 45 ml of thionyl chloride at 60° C. for 50 min, and then the mixture was concentrated under reduced pressure and the residue was taken up in methylene chloride. Insolubles were removed by filtration, and the methylene chloride solution was washed, dried over magnesium sulfate and concentrated under reduced pressure. The residue was taken up in 1 l of ether, active carbon was added, the mixture was filtered and the filtrate was concentrated to 100 ml. The product crystallized on cooling and was filtered off with suction and washed with cold ether. 9.1 g (=58%) of pure 6,7-dimethoxynaphthalene-2-sulfonyl chloride were obtained.

EXAMPLE 2 a) Preparation of dimethyl
N-(2-naphthalenesulfonyl)-L- or D-glutamate 28.4 g (134.2 mmol) of dimethyl L- or D-glutamate hydrochloride were introduced into 300 ml of methylene chloride. To this were successively added dropwise 70 ml (51.2 g, 505 mmol) of triethylamine and 25.8 g (113.8 mmol) of 2-naphthalenesulfonyl chloride dissolved in 100 ml of THF at 10°–15° C. The mixture was then stirred at room temperature for 1 h and subsequently concentrated under reduced pressure, the residue was taken up in ether/ethyl acetate, and the solution was washed first with dilute aqueous sulfamic acid solution and then several times with water and was dried over magnesium sulfate and concentrated under reduced pressure to give 33.4 g (76% of theory) of pure dimethyl N-(2-naphthalenesulfonyl)-L- or D-glutamate.

b) Preparation of N-(2-naphthalenesulfonyl)-L- or D-glutamic acid 29.5 g (80.7 mmol) of dimethyl N-(2-naphthalenesulfonyl)-L- or D-glutamate were dissolved in 500 ml of methanol and stirred with 170 ml (340 mmol) of 2N sodium hydroxide solution overnight. The pH was adjusted to 1 with concentrated hydrochloric acid, the solution was evaporated to dryness under reduced pressure, the residue was partitioned between a large volume of methylene chloride and a small volume of water, the methylene chloride phase was dried over magnesium sulfate and evaporated, and the residue was recrystallized from methylene chloride to give 20.3 g (75% of theory) of N-(2-naphthalenesulfonyl)-L- or D-glutamic acid as white solid.

c) Preparation of
3-[3-(2-naphthalenesulfonylamino)oxazolidin-5-on-4-yl]propionic acid 19.3 g (57.2 mmol) of N-(2-naphthalenesulfonyl)glutamic acid were heated together with 3.4 g (114.4 mmol) of paraformaldehyde, 0.5 g (4 mmol) of thionyl chloride and 6.1 g (60 mmol) of acetic anhydride in 140 ml of glacial acetic acid at 100° C. for 5 h. Since the reaction was incomplete, a further 3.4 g (114.4 mmol) of paraformaldehyde, 0.5 g (4 mmol) of thionyl chloride and 6.1 g (60 mmol) of acetic anhydride were added, and the mixture was heated at 100° C. for 8 h. The solvent was removed under reduced pressure, the residue was taken up in methylene chloride, and the solution was washed with water, dried over magnesium sulfate and concentrated under reduced pressure. The solid was washed several times with water to remove acetic acid. After drying, the product was extracted by boiling with diisopropyl ether, after which the filtrate was evaporated to yield 15.3 g (76% of theory) of almost pure 3-[3-(2-naphthalenesulfonylamino)oxazolidin- 5-on-4-yl]propionic acid.

d) Preparation of
3-[3-(2-naphthalenesulfonylamino)oxazolidin-5-on-4-yl]propanal 1.4 ml (18.2 mmol) of dry dimethylformamide were introduced into 50 ml of methylene chloride and, at 0° C. under an inert gas atmosphere, 2.0 ml (28.2 mmol) of oxalyl chloride in 70 ml of methylene chloride were added dropwise. The mixture was stirred at 0° C. for 30 min and then the solvent was removed under reduced pressure. The remaining white salt (highly hygroscopic) was suspended in 120 ml of THF/acetonitrile (1:1) and cooled to −30° C. To this were added dropwise 5.6 g (16 mmol) of 3-[3-(2-naphthalenesulfonylamino)oxazolidin-5-on- 4-yl]propionic acid together with 1.07 ml (16 mmol) of pyridine in 30 ml of THF, and the mixture was then stirred at −20° C. for 20 min. The mixture was subsequently cooled to −75° C., 307 mg of cuprous iodide were added, then a solution of 5.6 g (21.8 mmol) of lithium tri-tert-butoxyaluminum hydride in 20 ml of THF was slowly added dropwise, and the mixture was stirred at this temperature for 1 h. Quenching was then carried out at −75° C. with 30 ml of 2N hydrochloric acid and, after the mixture had warmed to room temperature, the solvent was removed under reduced pressure, the residue was taken up in methylene chloride, the Cu salts were removed by filtration, and the organic phase was washed three times with water, dried over magnesium sulfate and concentrated under reduced pressure. 5.4 g of slightly impure 3-[3-(2-naphthalenesulfonylamino)oxazolidin-5-on-4-yl]propanal were obtained which were rapidly processed further because of the low stability.

e) Preparation of 3-(2-naphthalenesulfonylamino)-1-[2-(4-cyanophenyl)-1-piperidinocarbonylethyl]-2-piperidinone 2.5 g (~7.5 mmol) of 3-[3-(2-naphthalenesulfonylamino)oxazolidin- 5-on-4-yl]propanal, as crude product, in 15 ml of methylene chloride, 2.2 g (7.5 mmol) of p-cyanophenylalaninylpiperidine hydrochloride in 15 ml of methylene chloride and 1.2 g (14.6 mmol) of sodium acetate were successively added to 7.5 g of freshly activated molecular sieves (4 Å) in 30 ml of methanol. The mixture was cooled to about 12° C. and then 0.9 g (14.3 mmol) of sodium cyanoborohydride dissolved in 20 ml of THF was added dropwise over the course of 35 min, and the mixture was stirred at room temperature for 3 h. The solids were then removed by filtration and washed with methylene chloride, the collected filtrates were evaporated under reduced pressure, the residue was taken up in ethyl acetate, and the solution was washed with dilute aqueous sulfamic acid solution (pH 1) and five times with saturated brine, dried over magnesium sulfate and evaporated under reduced pressure. Chromatography on silica gel (0.063–0.200 mm/eluent methylene chloride/methanol) resulted in 3.5 g (85% of theory over 3 stages) of pure 3-(2-naphthalenesulfonylamino)-1-[2-(4-cyanophenyl)- 1-piperidinocarbonylethyl]-2-piperidinone.

f) The subsequent reactions to prepare 3-(2-naphthalenesulfonylamino)-1-[2-(4-amidinophenyl)- 1-piperidinocarbonylethyl]-2-piperidinone were carried as in 1h, i and j.

EXAMPLE 3 a) Preparation of tert-butyl 2-(3-nitropyrid-2-on-1-yl)acetate 63.3 g (459 mmol) of powdered potassium carbonate were suspended in 100 ml of DMF and cooled to 0° C. and, at this temperature, a suspension of 21.5 g (153 mmol) of 2-hydroxy-3-nitropyridine in 100 ml of DMF was added. After stirring at 0° C. for 10 min, 23.6 ml (31.4 g, 161 mmol) of tert-butyl bromoacetate in 50 ml of DMF were added dropwise, and the mixture was then stirred for 45 min, during which an intense red coloration appeared. Potassium carbonate was filtered off with suction, the filtrate was acidified (pH 3) with aqueous hydrochloric acid and extracted with methylene chloride, and the organic phase was washed twice with water, dried over magnesium sulfate and evaporated. After adherent DMF and tert-butyl bromoacetate had been removed under high vacuum, the product was extracted by stirring with diisopropyl ether, resulting in 35.5 g (90% of theory) of tert-butyl 2-(3-nitropyrid-2-on-1-yl)acetate.

b) Preparation of 2-(3-nitropyrid-2-on-1-yl) acetic acid 35.5 g (140 mmol) of tert-butyl 2-(3-nitropyrid- 2-on-1-yl)acetate in 110 ml of methylene chloride were mixed with 107 ml (159.0 g, 1.40 mol) of trifluoroacetic acid and stirred at room temperature for 2 h. The mixture was concentrated under reduced pressure, the residue was stirred with diisopropyl ether, and the solid was filtered off with suction to yield 22.1 g (80% of theory) of 2-(3-nitropyrid- 2-on-1-yl)acetic acid.

c) Preparation of 2-(3-nitropyrid-2-on-1-yl)acetylpiperidine 10 g (50.5 mmol) of 2-(3-nitropyrid-2-on-1-yl)acetic acid were dissolved in 500 ml of THF, cooled to −20° C., 7 ml (6.7 g, 55.6 mmol) of pivaloyl chloride in 30 ml of THF and 7 ml (5.1 g, 50.5 mmol) of triethylamine in 30 ml of THF were added dropwise, and the mixture was then stirred at −20° C. for 20 min. Subsequently 5 ml (4.3 g, 50.5 mmol) of piperidine in 40 ml of THF were added dropwise, and the mixture was stirred at −20° C. for a further 30 min. The solution was acidified with 1N hydrochloric acid and extracted several times with methylene chloride, and the organic phase was washed with water, dried over magnesium sulfate and concentrated under reduced pressure. The residue was extracted by boiling with hexane several times and filtered hot. This resulted in 11.8 g (88% of theory) of 2-(3-nitropyrid-2-on-1-yl)acetylpiperidine which was still slightly impure with pivaloylpiperidine.

d) Preparation of 2-(3-aminopyrid-2-on-1-yl)acetylpiperidine hydrochloride 22.8 g (86 mmol) of 2-(3-nitropyrid-2-on- 1-yl)acetylpiperidine were dissolved in 460 ml of methanol, and 9.8 ml of (10.3 g, 172 mmol) of glacial acetic acid and 3.4 g of 10% palladium on active carbon were added, and the mixture was hydrogenated with hydrogen under slightly elevated pressure. After the reaction was complete, the catalyst was filtered off with suction and washed with methanol, and the filtrates were concentrated under reduced pressure. The residue was taken up in aqueous sulfamic acid solution, the aqueous phase was extracted twice with methylene chloride (contains mainly pivaloylpiperidine) then made alkaline and extracted four times with methylene chloride and the extracts were dried over magnesium sulfate, acidified with ethereal hydrochloric acid and concentrated under reduced pressure to give 14.2 g (61% of theory) of 2-(3-aminopyrid-2-on-1-yl)acetylpiperidine hydrochloride.

e) Preparation of 2-[3-(2-naphthalenesulfonylamino)pyrid-2-on-1-yl]acetylpiperidine 10.3 g (45.5 mmol) of 2-naphthalenesulfonyl chloride in 100 ml of methylene chloride were added dropwise to a solution of 14.2 g (53.5 mmol) of 2-(3-aminopyrid- 2-on-1-yl)acetylpiperidine hydrochloride and 43.2 ml (42.3 g, 535 mmol) of pyridine in 250 ml of methylene chloride, and the mixture was stirred at room temperature for 1.5 h. The solution was then acidified with 1N hydrochloric acid, and the organic phase was washed once with water, dried over magnesium sulfate and concentrated under reduced pressure to give 18.4 g (95% of theory) of 2-[3-(2-naphthalenesulfonylamino)pyrid-2-on- 1-yl]acetylpiperidine.

f) Preparation of 2-[3-(2-naphthalenesulfonyl(tert-butyloxycarbonyl) amino)pyrid- 2-on -1-yl]acetylpiperidine 18.4 g (43 mmol) of 2-[3-(2-naphthalenesulfonylamino)pyrid- 2-on-1-yl]acetylpiperidine were dissolved in 300 ml of methylene chloride and, successively, 9.4 g (43 mmol) of di-tert-butyl dicarbonate and 5.3 g (43 mmol) of dimethylaminopyridine were added, resulting in a homogeneous solution which was then stirred for 40 min. The solution was subsequently adjusted to pH 2.5 with 1N hydrochloric acid, and the organic phase was washed once with water, dried over magnesium sulfate and evaporated under reduced pressure. Extraction by stirring with hexane resulted in 22.0 g (97.3% of theory) of 2-[3-(2-naphthalenesulfonyl(tert-butyloxycarbonyl)amino)pyrid- 2-on-1-yl]acetylpiperidine.

g) Preparation of 3-(2-naphthalenesulfonyl(tert-butyloxycarbonyl)amino)-1-[2-(4-cyanophenyl)-1-piperidinocarbonylethyl]-2-piperidone 6.1 ml (10.14 mmol) of 15% strength butyllithium solution in hexane, 4.1 g (7.8 mmol) of 2-[3-(2-naphthalenesulfonyl(tert-butyloxycarbonyl)amino)pyrid- 2-on-1-yl] acetylpiperidine in 40 ml of THF and 1.4 g (7.02 mmol) of p-cyanobenzyl bromide in 30 ml of THF were successively added dropwise to 1.4 ml (1.03 g, 10.14 mmol) of diisopropylamine in 40 ml of THF at −70° C. The mixture was stirred at −70° C. for 2 h and then allowed to warm to room temperature, methylene chloride was added, the pH was adjusted to 2.5 with 1N hydrochloric acid, and the aqueous phase was extracted. The organic phase was washed with water, dried over magnesium sulfate and concentrated under reduced pressure. The resulting crude product was purified by column chromatography (silica gel 0.063–0.200 mm, eluent: methylene chloride/methanol). 2.5 g (56% of theory) of 3-(2-naphthalenesulfonyl(tert-butyloxycarbonyl)amino)-1-[2-(4-cyanophenyl)-1-piperidinocarbonylethyl]- 2-piperidone were obtained.

h)
3-(2-Naphthalenesulfonyl(tert-butyloxycarbonyl)amino)-1-[2-(4-amidinophenyl)-1-piperidinocarbonylethyl]-2-pyridone was prepared in a similar way to 1h, i and j. After elimination of the Boc protective group (trifluoroacetic acid/methylene chloride), the 3-(2-naphthalenesulfonylamino)-1-[(2-(4-amidinophenyl)- 1-piperidinocarbonylethyl]-2-pyridone was obtained as trifluoroacetate.

The following can be prepared in a similar way to Examples 1 to 3:

4) 3-(2-Naphthalenesulfonylamino)-1-[2-(4-amidinophenyl)-1-piperidinocarbonylethyl]-2-pyrrolidinone 5) 3-(2-Naphthalenesulfonylamino)-1-[2-(4-amidinophenyl)-1-ethoxycarbonylethyl]-2-piperidinone 6) 3-(2-Naphthalenesulfonylamino)-1-[2-(4-amidinophenyl)- 1-carboxyethyl]-2-piperidinone 7) 3-(2-Naphthalenesulfonylamino)-1-[2-(4-amidinophenyl)-1-ethoxycarbonylethyl]-2-pyrrolidinone 8) 3-(2-Naphthalenesulfonylamino)-1-[2-(4-amidinophenyl)- 1-carboxyethyl]-2-pyrrolidinone 9) 3-(2-Naphthalenesulfonylamino)-1-[2-(4-amidinophenyl)- 1-ethoxycarbonylethyl]-2-pyridone 10) 3-(2-Naphthalenesulfonylamino)-1-[2-(4-amidinophenyl)- 1-carboxyethyl]-2-pyridone 11) 3-(4-Methoxynaphthalene-2-sulfonylamino)-1-[2-(4-amidinophenyl)-1-piperidinocarbonylethyl]-2-piperidinone 12) 3-(4-Methoxynaphthalene-2-sulfonylamino)-1-[2-(4-amidinophenyl)-1-ethoxycarbonylethyl]-2-piperidinone 13) 3)
3-(4-Methoxynaphthalene-2-sulfonylamino)-1-[2-(4-amidinophenyl)-1-carboxyethyl]-2-piperidinone 14) 3-(4-Methoxynaphthalene -2-sulfonylamino)-1-[2-(4-amidinophenyl)-1-piperidinocarbonylethyl]-2-pyrrolidinone 15) 3-(4-Methoxynaphthalene-2-sulfonylamino)-1-[2-(4-amidinophenyl)-1-ethoxycarbonylethyl]-2-pyrrolidinone 16) 3-(4-Methoxynaphthalene-2-sulfonylamino)-1-[2-(4-amidinophenyl)-1-carboxyethyl]-2-pyrrolidone 17) 3-(4-Methoxynaphthalene-2-sulfonylamino)-1-[2-(4-amidinophenyl)-1-piperidinocarbonylethyl] -piperid-2-one 18) 3-(4-Methoxynaphthalene-2-sulfonylamino)-1-[2-(4-amidinophenyl)-1-ethoxycarbonylethyl] -piperid-2-one 19) 3-(4-Methoxynaphthalene-2-sulfonylamino)-1-[2-(4-amidinophenyl)-1-carboxyethyl]-piperid-2-one 20) 3-(6-Methoxynaphthalene-2-sulfonylamino)-1-[2-(4-amidinophenyl)-1-piperidinocarbonylethyl]-2-piperidinone 21) 3-(6-Methoxynaphthalene-2-sulfonylamino)-1-[2-(4-amidinophenyl)-1-ethoxycarbonylethyl]-2-piperidinone 22) 3-(6-Methoxynaphthalene-2-sulfonylamino)-1-[2-(4-amidinophenyl)-1-carboxyethyl]-2-piperidinone 23) 3-(6-Methoxynaphthalene-2-sulfonylamino)-1-[2-(4-amidinophenyl)-1-piperidinocarbonylethyl]-2-pyrrolidinone 24) 3-(6-Methoxynaphthalene-2-sulfonylamino)-1-[2-(4-amidinophenyl)-1-ethoxycarbonyl ethyl]-2-pyrrolidinone 25) 3-(6-Methoxynaphthalene-2-sulfonylamino)-1-[2-(4-amidinophenyl)-1-carboxyethyl]-2-pyrrolidinone 26) 3-(6-Methoxynaphthalene-2-sulfonylamino)-1-[2-(4-amidinophenyl)-1-piperidinocarbonylethyl]-piperid- 2-one 27) 3-(6-Methoxynaphthalene-2-sulfonylamino)-1-[2-(4-amidinophenyl)-1-ethoxycarbonylethyl] -piperid-2-one 28) 3-(6-Methoxynaphthalene-2-sulfonylamino)-1-[2-(4-amidinophenyl)-1-carboxyethyl]-piperid -2-one 29) 3-(7-Methoxynaphthalene-2-sulfonylamino)-1-[2-(4-amidinophenyl)-1-piperidinocarbonylethyl]-2-piperidinone 30) 3-(7-Methoxynaphthalene-2-sulfonylamino)-1-[2-(4-amidinophenyl)-1-ethoxycarbonylethyl]-2-piperidinone 31) 3-(7-Methoxynaphthalene-2-sulfonylamino)-1-[2-(4-amidinophenyl)-1-carboxyethyl]-2-piperidinone 32) 3-(7-Methoxynaphthalene-2-sulfonylamino)-1-[2-(4-amidinophenyl)-1-piperidinocarbonylethyl]-2-pyrrolidinone 33) 3-(7-Methoxynaphthalene-2-sulfonylamino)-1-[2-(4-amidinophenyl)-1-ethoxycarbonylethyl]-2-pyrrolidinone 34) 3-(7-Methoxynaphthalene-2-sulfonylamino)-1-[2-(4-amidinophenyl)-1-carboxyethyl]-2-pyrrolidinone 35) 3-(7-Methoxynaphthalene-2-sulfonylamino)-1-[2-(4-amidinophenyl)-1-piperidinocarbonylethyl]-piperid-2-one 36) 3-(7-Methoxynaphthalene-2-sulfonylamino)-1-[2-(4-amidinophenyl)-1-ethoxycarbonylethyl]-piperid-2-one 37) 3-(7-Methoxynaphthalene-2-sulfonylamino)-1-[2-(4-amidinophenyl)-1-carboxyethyl]-2-piperid-2-one 38) 3-(6,7-Dimethoxynaphthalene-2-sulfonylamino)-1-[2-(4-amidinophenyl)-1-piperidinocarbonylethyl]-2-piperidinone 39) 3-(6,7-Dimethoxynaphthalene-2-sulfonylamino)-1-[2-(4-amidinophenyl)-1-ethoxycarbonylethyl]-2-piperidinone 40) 3-(6,7-Dimethoxynaphthalene-2-sulfonylamino)-1-[2-(4-amidinophenyl)-1-carboxyethyl]-2-piperidinone 41) 3-(6,7-Dimethoxynaphthalene-2-sulfonylamino)-1-[2-(4-amidinophenyl)-1-piperidinocarbonylethyl]-2-pyrrolidinone 42) 3-(6,7-Dimethoxynaphthalene-2-sulfonylamino)-1-[2-(4-amidinophenyl)-1-ethoxycarbonylethyl]-2-pyrrolidinone 43) 3-(6,7-Dimethoxynaphthalene-2-sulfonylamino)-1-[2-(4-amidinophenyl)-1-carboxyethyl]-2-pyrrolidinone 44) 3-(6,7-Dimethoxynaphthalene-2-sulfonylamino)-1-[2-(4-amidinophenyl)-1-piperidinocarbonylethyl]-piperid-2-one 45) 3-(6,7-Dimethoxynaphthalene-2-sulfonylamino)-1-[2-(4-amidinophenyl)-1-ethoxycarbonylethyl]-piperid-2-one 46) 3-(6,7-Dimethoxynaphthalene-2-sulfonylamino)-1-[2-(4-amidinophenyl)-1-carboxyethyl]-piperid-2-one 47) 3-(4,6-Dimethoxynaphthalene-2-sulfonylamino)-1-[2-(4-amidinophenyl)-1-piperidinocarbonylethyl]-2-piperidinone 48) 3-(4,6-Dimethoxynaphthalene-2-sulfonylamino)-1-[2-(4-amidinophenyl)-1-ethoxycarbonylethyl]-2-piperidinone 49) 3-(4,6-Dimethoxynaphthalene-2-sulfonylamino)-1-[2-(4-amidinophenyl)-1-carboxyethyl]-2-piperidinone 50) 3-(4,6-Dimethoxynaphthalene-2-sulfonylamino)-1-[2-(4-amidinophenyl)-1-piperidinocarbonylethyl]-2-pyrrolidinone 51) 3-(4,6-Dimethoxynaphthalene-2-sulfonylamino)-1-[2-(4-amidinophenyl)-1-ethoxycarbonylethyl]-2-pyrrolidinone 52) 3-(4,6-Dimethoxynaphthalene-2-sulfonylamino)-1-[2-(4-amidinophenyl)-1-carboxyethyl]-2-pyrrolidinone 53) 3-(4,6-Dimethoxynaphthalene-2-sulfonylamino)-1-[2-(4-amidinophenyl)-1-piperidinocarbonylethyl]-piperid-2-one 54) 3-(4,6-Dimethoxynaphthalene-2-sulfonylamino)-1-[2-(4-amidinophenyl)-1-ethoxycarbonylethyl]-piperid-2-one 55) 3-(4,6-Dimethoxynaphthalene-2-sulfonylamino)-1-[2-(4-amidinophenyl)-1-carboxyethyl]-piperid-2-one 56) 3-(6,7-Dimethoxynaphthalene-2-sulfonylamino)-1-[2-(4-amidinophenyl)-1-pyrrolidinocarbonylethyl]-2-piperidinone 57) 3-(6,7-Dimethoxynaphthalene-2-sulfonylamino)-1-[2-(4-amidinophenyl)-1-morpholinocarbonylethyl]-2-piperidinone 58) 3-(6,7-Dimethoxynaphthalene-2-sulfonylamino)-1-[2-(4-amidinophenyl)-1-hexahydroazepinocarbonylethyl]-2-piperidinone 59) 3-(6,7-Dimethoxynaphthalene-2-sulfonylamino)-1-[2-(4-amidinophenyl)-1-pyrrolidinocarbonylethyl]-2-pyrrolidinone 60) 3-(6,7-Dimethoxynaphthalene-2-sulfonylamino)-1-[2-(4-amidinophenyl)-1-morpholinocarbonylethyl]-2-pyrrolidinone 61) 3-(6,7-Dimethoxynaphthalene-2-sulfonylamino)-1-[2-(4-amidinophenyl)-1-hexahydroazepinocarbonylethyl]-2-pyrrolidinone 62) 3-(6,7-Methylenedioxynaphthalene-2-sulfonylamino)-1-[2-(4-amidinophenyl)-1-piperidinocarbonylethyl]-2-piperidinone 63) 3-(6,7-Methylenedioxynaphthalene-2-sulfonylamino)-1-[2-(4-amidinophenyl)-1-ethoxycarbonylethyl]-2-piperidinone 64) 3-(6,7-Methylenedioxynaphthalene-2-sulfonylamino)-1-[2-(4-amidinophenyl)-1-carboxyethyl]-2-piperidinone 65) 3-(6,7-Methylenedioxynaphthalene-2-sulfonylamino)-1-[2-(4-amidinophenyl)-1-piperidinocarbonylethyl]-2-pyrrolidinone 66) 3-(6,7-Methylenedioxynaphthalene-2-sulfonylamino)-1-[2-(4-amidinophenyl)-1-ethoxycarbonylethyl]-2-pyrrolidinone 67) 3-(6,7-Methylenedioxynaphthalene-2-sulfonylamino)-1-[2-(4-amidinophenyl)-1-carboxyethyl]-2-pyrrolidinone 68) 3-(6,7-Ethylenedioxynaphthalene-2-sulfonylamino)-1-[2-(4-amidinophenyl)-1-piperidinocarbonylethyl]-2-piperidinone 69) 3-(6,7-Ethylenedioxynaphthalene-2-sulfonylamino)-1-[2-(4-amidinophenyl)-1-piperidinocarbonylethyl]-2-pyrrolidinone

We claim:

1. A 2-substituted 3-(4-amidinophenyl) propionic acid of the formula

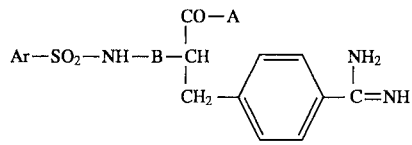

where
A is

or $-OR^3$ in which $R^1$ and $R^2$, which can be identical or different, are each hydrogen, alkyl or alkenyl with up to 6 carbons, or $R^1$ and $R^2$ together with the nitrogen to which they are bonded are a 5-to 7-membered saturated ring which is unsubstituted or substituted by alkyl radicals with up to 4 carbons and can contain an oxygen atom, where the nitrogen and oxygen atoms are in the 1,2 or 1,4 positions, and where $R^3$ is hydrogen, alkyl or alkenyl with up to 6 carbons, B is

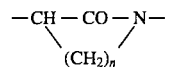

(where n is 1, 2, 3, 4 or 5) or

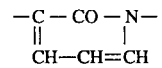

Ar is phenyl or α- or β-naphthyl which is unsubstituted or substituted by one or more halogen atoms, nitro groups, amino groups, $C_{1-4}$-mono- or bisalkylamino groups, hydroxyl groups, $C_{1-4}$-alkoxy groups, a methylenedioxy or ethylenedioxy radical, or Ar is pyridyl, quinolyl or isoquinolyl which is unsubstituted or substituted by one or more $C_{1-4}$-alkyl groups or $C_{1-4}$-alkoxy groups, and the salts thereof with physiologically tolerated acids.

2. The 2-substituted 3-(4-amidinophenyl)propionic acid of claim 1, wherein
A is

where $R^1$ and $R^2$ together with the nitrogen atom are a 5-to 7-membered ring which may be substituted by $C_1$–$C_4$-alkyl radicals;

B is a pyrrolidone, a piperidinone or a piperidone group; and

Ar is β-naphthyl which is substituted by one or more $C_1$–$C_4$-alkoxy radicals.

3. The 2-substituted 3-(4-amidinophenyl)proprionic acid of claim 2, wherein

Ar is β-naphthyl which is substituted by one or two methoxy groups in position 4, 5, 6, 7 and/or 8 by a methylene dioxy or ethylenedioxy radical.

4. A method of treating thromboembolic disorders in a patient in need thereof which comprises administering to the patient an effective amount of a 2-substituted 3-(4-amidinophenyl)propionic acid as defined in claim 1.

* * * * *

UNITED STATES PATENT AND TRADEMARK OFFICE
CERTIFICATE OF CORRECTION

PATENT NO.: 5,489,583

DATED: February 6, 1996

INVENTOR(S): MACK et al.

It is certified that error appears in the above-identified patent and that said Letters Patent is hereby corrected as shown below:

On the title page, item [30], "41 20 947.3" should be --41 21 947.3--.

Signed and Sealed this

Ninth Day of April, 1996

Attest:

BRUCE LEHMAN

Attesting Officer

Commissioner of Patents and Trademarks